United States Patent
Krohn

(10) Patent No.: US 9,190,966 B2
(45) Date of Patent: Nov. 17, 2015

(54) IMPEDANCE BOOTSTRAP CIRCUIT FOR AN INTERFACE OF A MONITORING DEVICE

(71) Applicant: Stryker Corporation, Kalamazoo, MI (US)

(72) Inventor: Randall Jeffrey Krohn, Wildwood, MO (US)

(73) Assignee: STRYKER CORPORATION, Kalamazoo, MI (US)

( * ) Notice: Subject to any disclaimer, the term of this patent is extended or adjusted under 35 U.S.C. 154(b) by 234 days.

(21) Appl. No.: 13/899,948

(22) Filed: May 22, 2013

(65) Prior Publication Data

US 2013/0328627 A1    Dec. 12, 2013

Related U.S. Application Data

(60) Provisional application No. 61/650,119, filed on May 22, 2012.

(51) Int. Cl.
| | |
|---|---|
| *H03F 3/45* | (2006.01) |
| *H03F 1/56* | (2006.01) |
| *A61B 5/00* | (2006.01) |
| *A61B 5/04* | (2006.01) |

(52) U.S. Cl.
CPC .............. *H03F 1/56* (2013.01); *A61B 5/04004* (2013.01); *A61B 5/7203* (2013.01); *H03F 3/45968* (2013.01); *H03F 2200/261* (2013.01); *H03F 2203/45138* (2013.01)

(58) Field of Classification Search
USPC .......................................... 330/258, 302, 306
IPC ....................................................... H03F 3/45
See application file for complete search history.

(56) References Cited

U.S. PATENT DOCUMENTS

| | | | |
|---|---|---|---|
| 4,191,195 A | 3/1980 | Miller | |
| 4,320,351 A | 3/1982 | Brown, Jr. et al. | |
| 5,300,896 A | 4/1994 | Suesserman | |
| 5,410,274 A * | 4/1995 | Birdsall et al. | 330/265 |
| 5,427,111 A | 6/1995 | Traub et al. | |
| 5,568,561 A * | 10/1996 | Whitlock | 381/120 |
| 6,078,215 A * | 6/2000 | Fiori, Jr. | 330/69 |
| 6,208,888 B1 * | 3/2001 | Yonce | 600/509 |
| 6,866,639 B2 | 3/2005 | Causevic et al. | |
| 6,950,694 B2 | 9/2005 | Yonce | |
| 2005/0077928 A1 * | 4/2005 | Honda et al. | 327/112 |

(Continued)

OTHER PUBLICATIONS

Linear Technology Corporation,Single Resistor Gain Programmable, Precision Instrumentation Amplifier Datasheet, 1167fa LT/TP 0301 2K Rev. A, 1998; 20 pages.

Web page <http://www.x2y.com/techsummary.htm>, Jun. 2011, Retrieved from Internet Archive Wayback Machine <http://web.archive.org/web/20110701000925/http://www.x2y.com/techsummary.htm>; 3 pages.

(Continued)

*Primary Examiner* — Patricia T Nguyen
(74) *Attorney, Agent, or Firm* — Howard & Howard Attorneys PLLC

(57) ABSTRACT

An interface for receiving electrical signals representative of a condition of a patient and for conveying representations of the electrical signals to a processing system. The interface includes at least one amplifier circuit configured to alter an amplitude of the electrical signal, a common-mode cancellation amplifier circuit coupled to the at least one amplifier circuit and configured to reduce common-mode signal noise in the electrical signals, and a bootstrap circuit coupled to the at least one amplifier circuit and configured to increase an effective input impedance at an input of the at least one amplifier circuit.

15 Claims, 10 Drawing Sheets

(56) References Cited

U.S. PATENT DOCUMENTS

| | | | |
|---|---|---|---|
| 2006/0034621 A1* | 2/2006 | Denoyer | 398/208 |
| 2006/0048880 A1 | 3/2006 | Blessing et al. | |
| 2007/0167694 A1 | 7/2007 | Causevic et al. | |
| 2008/0243021 A1 | 10/2008 | Causevic et al. | |
| 2009/0309605 A1 | 12/2009 | Prance et al. | |
| 2013/0266156 A1* | 10/2013 | Frohlich et al. | 381/120 |

OTHER PUBLICATIONS

National Semiconductor Corp., FET Circuit Applications, Application Note AN-32 Figure TL/H/6791-4 (Feb. 1970) 1995; 14 pages.

Walt Jung, Analog Devices, Bootstrapped IC Substrate Lowers Distortion in JFET Op Amps, Application Note, AN-232, Figure 1, Audio Products pp. 4-73-4-76 (Jul. 1992).

* cited by examiner

IMPEDANCE BOOTSTRAP CIRCUIT FOR AN INTERFACE OF A MONITORING DEVICE

CROSS-REFERENCE TO RELATED APPLICATIONS

This application claims benefit of U.S. Provisional Patent Application No. 61/650,119, filed on May 22, 2012, the entirety of which is hereby incorporated herein by reference.

BACKGROUND

1. Field of the Invention

The subject invention relates generally to a device for monitoring the level of consciousness of a patient under anesthesia, and more particularly, to a device that includes an interface circuit configured to reduce signal noise and radio frequency (RF) interference susceptibility.

2. Description of the Related Art

There is an emerging field for devices used to assist medical personnel in monitoring a patient's response to anesthesia and level of sedation during surgical procedures. The devices are configured to receive and process bio-electric signals from real-time brain activity in patients under sedation. The bio-electric signals are generally low voltage electrical signals in the sub-microvolt range, and are measured using a plurality of physiological sensors (e.g., electrodes) placed on the forehead of the patient. These low voltage signals can be extremely difficult to detect due to signal noise and RF interference that often mask the desired signals.

The device, referred to hereinafter as a monitoring device, includes among other components, an analog interface configured to receive and process the detected bio-electric signals prior to transmitting the resultant signals to an internal processor for further processing. Like any device that houses multiple electrical components in relative close proximity, the monitoring device is susceptible to signal noise and RF interference generated from a variety of sources. One such signal noise source is low-frequency noise, primarily from U.S. line frequencies, which can be capacitively coupled to the patient and to the monitoring device through building infrastructure, power cords, and other patient-connected equipment. RF interference may be presented to the device through radiated or conducted means, and can be generated by equipment in the operating room (such as electrosurgical generators and patient monitoring equipment) or by radio transceivers (such as cell phones, pagers, RF tracking systems). Consequently, signal noise and aliased RF interference may be present in the critical bandwidth of the bio-electric signals being analyzed; thereby adversely affecting the accuracy of the monitoring device.

One known technique for addressing noise and RF interference introduced into the critical bandwidth is common-mode cancellation. For example, U.S. Patent Application No. 2008/0243021 discloses an analog interface that includes a common-mode cancellation circuit that outputs a reference signal for cancelling common-mode voltage present at the electrodes. In other words, the cancellation circuit filters the incoming low voltage electrical signals.

Though common-mode cancellation is an effective technique, there remains an opportunity to provide an improved analog interface that further increases the monitoring device's immunity to signal noise and RF interference.

SUMMARY

An interface is provided for receiving electrical signals representative of a condition of a patient and for conveying representations of the electrical signals to a processing system. The interface includes at least one amplifier circuit configured to alter an amplitude of the electrical signal, a common-mode cancellation amplifier circuit coupled to the at least one amplifier circuit and configured to reduce common-mode signal noise in the electrical signals, and a bootstrap circuit coupled to the at least one amplifier circuit and configured to increase an effective input impedance at an input of the at least one amplifier circuit.

Accordingly, the interface increases immunity of the interface to signal noise and RF interference thereby increasing accuracy of patient monitoring by the monitoring device.

BRIEF DESCRIPTION OF THE DRAWINGS

Advantages of the present invention will be readily appreciated, as the same becomes better understood by reference to the following detailed description when considered in connection with the accompanying drawings wherein.

DETAILED DESCRIPTION

Figure 1:
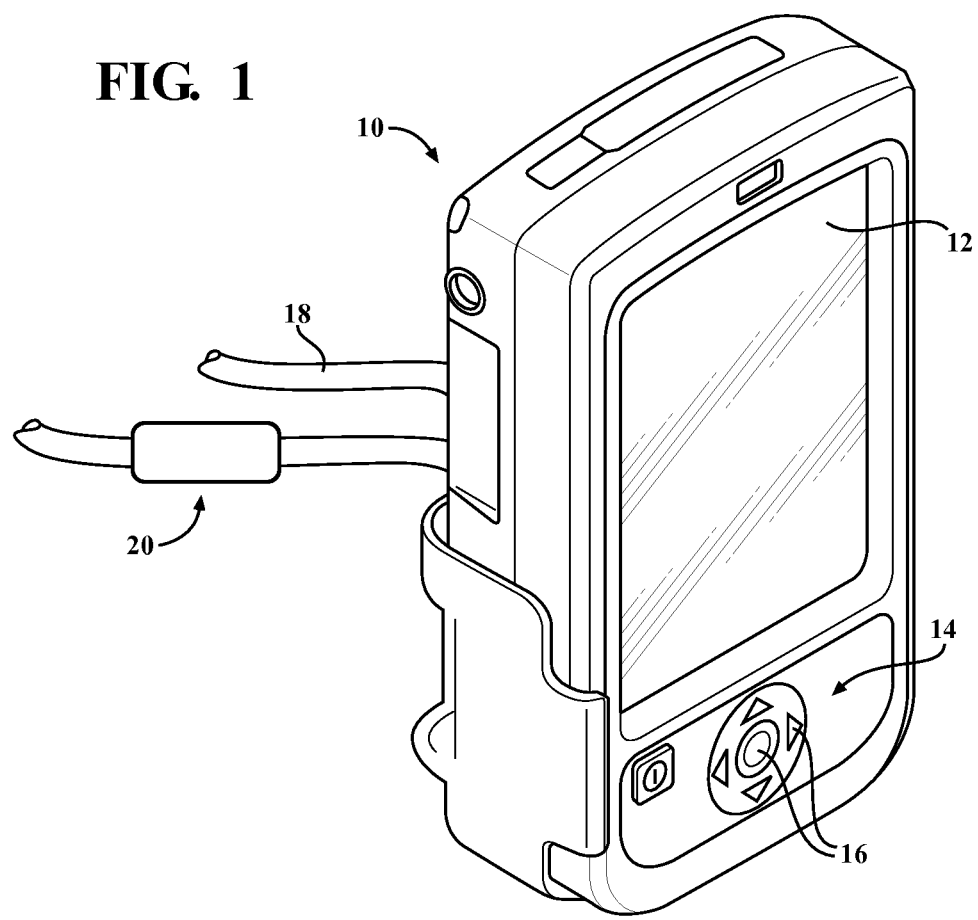
FIG. 1 illustrates a monitoring device according to an embodiment of the present invention.

Referring to the Figures, wherein like numerals indicate like or corresponding parts throughout the several views, a device for monitoring a level of consciousness in patients under anesthesia is generally shown at 10 in FIG. 1. The device 10, referred to hereinafter as a monitoring device, is a self-contained portable device used by medical personnel to monitor the patient's level of consciousness during sedation. In one embodiment, the monitoring device 10 is battery powered and handheld, but may also be incorporated into other patient monitoring equipment.

The monitoring device 10 is configured to provide a quantitative measure of a patient's level of consciousness. In one embodiment, this quantization is characterized by an index that varies, for example, between 0 and 99, where 0 indicates deep sedation and 99 indicates an awake patient. An exemplary device for monitoring a patient's level of consciousness is disclosed in U.S. Patent Application No. 2007/0167694 (hereinafter the '694 application), which is hereby incorporated by reference in its entirety.

Like the device in the '694 application, the monitoring device 10 includes a display 12 and a control section 14, which includes a plurality of keys 16 used to navigate and control the functionality of the monitoring device 10. In some cases, the monitoring device 10 is used in conjunction with a larger patient monitoring system that generally includes a host computer (not shown). The monitoring device 10 communicates with the host computer through a universal host bus, or other suitable communication means, as indicated for example by cable 18. One of ordinary skill in the art understands that any means of communications with the host computer are within the scope of the invention including means that do not utilize cable 18.

To determine the patient's level of consciousness, the monitoring device 10 receives and processes bio-electric signals detected using a plurality of physiological sensors affixed to the patient's forehead. The bio-electric signals are extremely low voltage electrical signals that represent the patient's real-time brain activity. Ultimately, the bio-electric signals are transmitted to an internal processor in the monitoring device 10 through a patient interface cable (PIC) assembly 20.

Because many high-frequency and high-energy devices are routinely applied to patients during surgical procedures, the RF interference and signal noise generated by these devices often couples to the patient. If not properly attenuated, this noise and interference can be aliased into the signal bandwidth used to determine the patient's level of consciousness index. This inadvertent aliasing can result in a disruption of the monitoring process, or worse, the aliased artifact can be included in the signal analyzed by the monitoring device, leading to an inaccurate index value.

Prior to being received by the processor in the monitoring device 10, the bio-electric signals are processed by an interface circuit, which includes an instrumentation amplifier to increase the amplitude of the difficult to detect low voltage bio-electric signals. To address the aliasing of signal noise and RF interference into the signal bandwidth of interest, the interface circuit further includes a bootstrapping network configured to reduce the electrical noise introduced into the bio-electric signals. As described in detail below, the bootstrapping network increases the effective input impedance of the instrumentation amplifier; thereby reducing mode conversion with patient electrode impedance mismatches.

As understood by one of ordinary skill in the art, the interface circuit may be a stand-alone device or incorporated into one of the monitoring system components. For example, in one embodiment, the interface circuit may be enclosed within the monitoring device 10. In an alternative embodiment, the interface circuit may be incorporated within the PIC cable assembly 20 or PIC connector.

Figure 2:
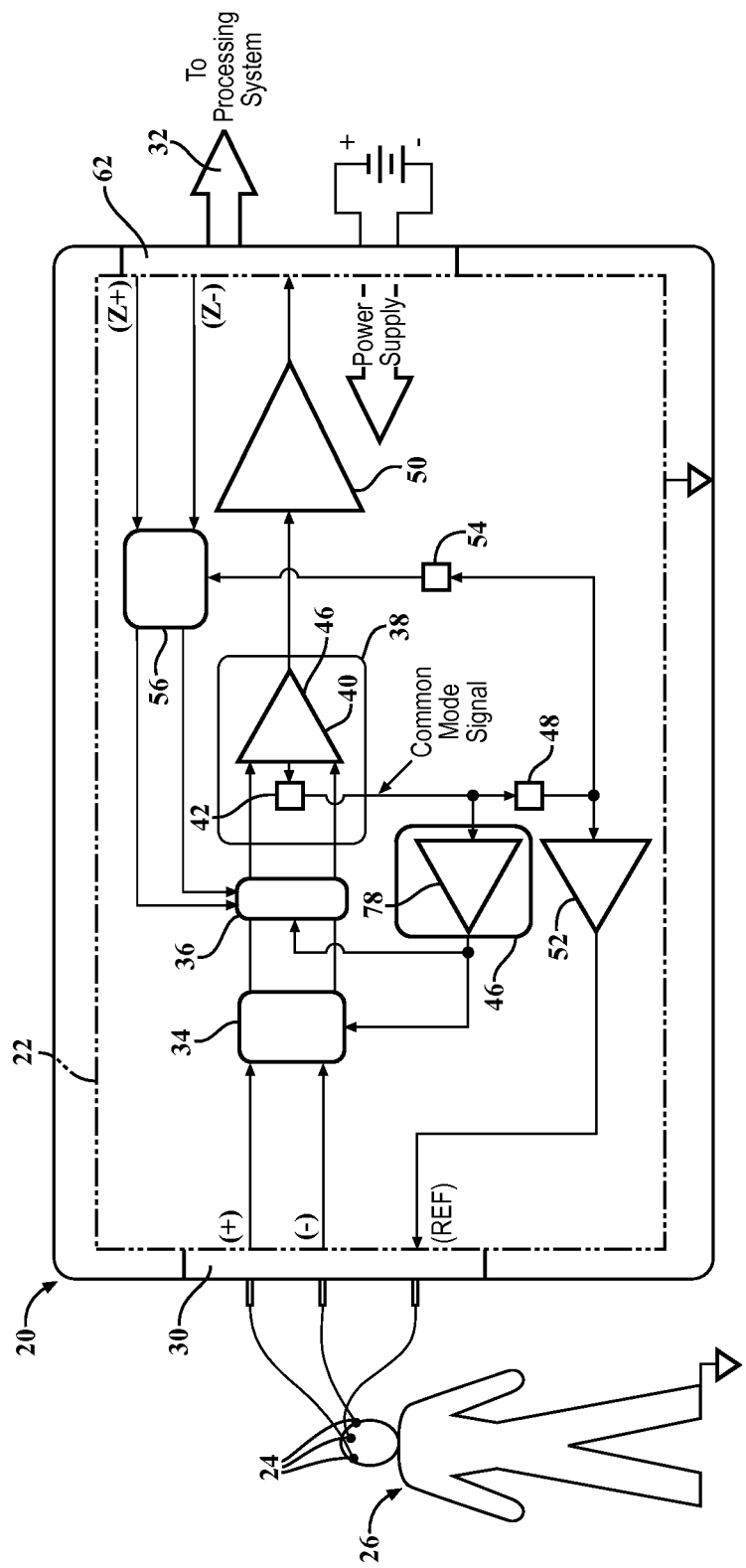
FIG. 2 illustrates an analog interface according to an embodiment of the present invention.

FIG. 2 illustrates a diagram of an exemplary interface circuit 22 coupled to a plurality of physiological sensors 24 affixed to a patient's 26 forehead. As shown, there are three sensors 24 being used to monitor the patient's brain activity. However, it should be appreciated that the sensors 24 shown in FIG. 2 are merely exemplary in that any number, type or configuration of sensors may be used without departing from the scope of the invention. Moreover, the bio-electric signals are generally electroencephalography (EEG) signals; however, one of ordinary skill in the art understands that the bio-electric signals may be any signal suitable for evaluation by the monitoring device 10, such as, but not limited to, electrocardiography (ECG) signals.

As set forth above, the bio-electric signals are low voltage electrical signals in the sub-microvolt range, which are highly susceptible to signal noise and RF interference. These low voltage signals also have uncontrolled and variable input impedances. Unlike line receivers, such as audio-line receivers that have predetermined and controlled input impedances, the impedances between the sensors 24 and the scalp of the patient 26 are naturally complex and variable and range from approximately 10 kΩ to 100 kΩ. As a point of reference, the bio-electric signals have a frequency band of interest with respect to the monitoring of the patient 26 that generally ranges between 2-480 Hz.

Figure 3:
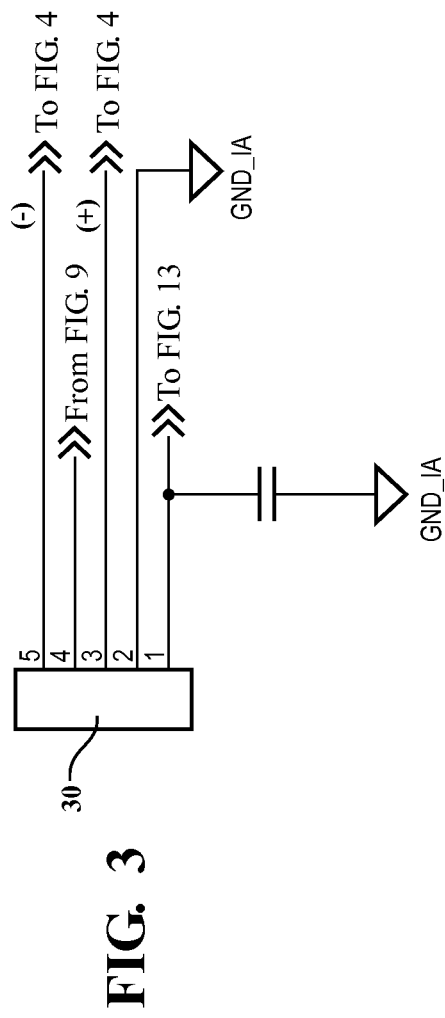
FIG. 3 illustrates a circuit diagram of a front-end connector of the interface according to an embodiment of the present invention.

The bio-electric signals transmitted from the sensors 24 are presented as differential signals (+) and (−) to a front-end connector 30 of the interface circuit 22. FIG. 3 depicts a schematic illustrating the connections between the front-end connector 30 and other components of the interface circuit 22. Note that, with the exception of pin 2 connecting to ground, each of the pin connections of the front-end connector 30 provide a reference to another Figure. Thus, a description of the components associated with each of those pin connections will be discussed in detail as set forth below in connection with each of the referenced Figures.

Figure 4:
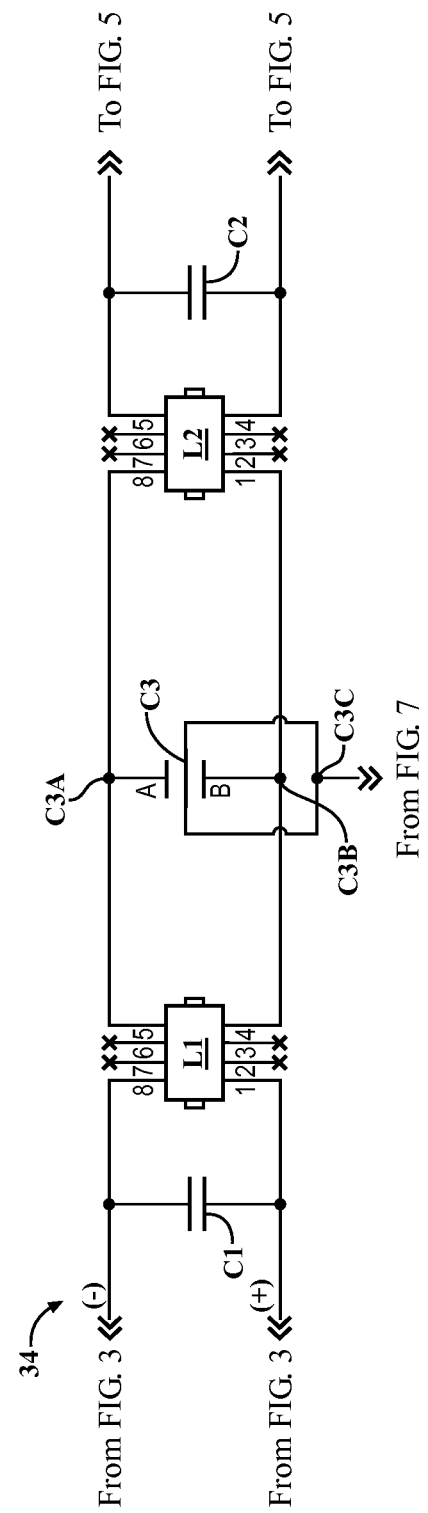
FIG. 4 illustrates a circuit diagram of an input filter circuit of the interface according to an embodiment of the present invention.

Returning to FIG. 2, the interface circuit 22 includes an input filter circuit 34 for reducing differential and common-mode radio frequency interference present in the bio-electric signals. The input filter circuit 34 is configured to receive the differential bio-electric signals from pins 3 and 5 of the front-end connector 30. As shown in FIG. 4, the input filter circuit 34 includes two asymmetric digital subscriber loop (ADSL) filters, L1 and L2, each connected in parallel to capacitors C1 and C2, respectively. Coupled between filters L1 and L2, is a capacitive component C3, which in one embodiment, is a balanced capacitor having opposing electrode layers stacked inside a conventional bypass capacitor for filtering electromagnetic interference in the electrical signal. In one specific, non-limiting example, capacitor C3 is a X2Y® capacitor, which is an ultra-low inductance three-node capacitor circuit consisting of two balanced Y capacitors of equal value. This configuration enables filtering of two signal lines (or positive and negative power lines) simultaneously and provides broadband filtering characteristics for both differential and common-mode noise signals into the GHz band. Using a X2Y® capacitor as shown in FIG. 4, a first node C3A of capacitor C3 is connected to pins 5 and 8, respectively, of filters L1 and L2. A second node C3B of capacitor C3 is connected to pins 4 and 1, respectively, of filters L1 and L2. In this configuration, the input filter circuit 34 provides a low-pass corner at approximately 30 KHz. The output of the input filter circuit 34, and more particularly, the output of filter L2, is directly coupled to a low pass filter circuit 36, which is shown in block form in FIG. 2, and illustrated schematically in FIG. 5.

Figure 5:
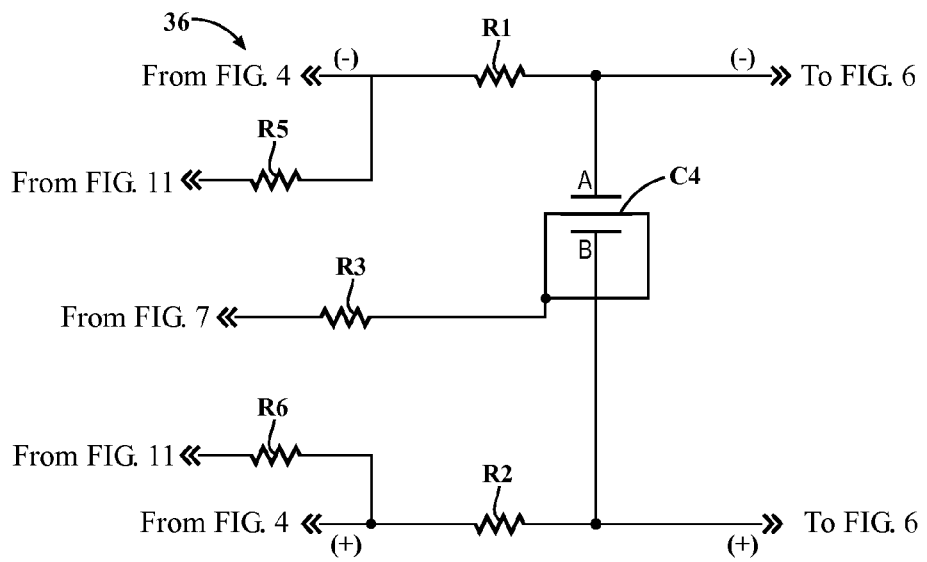
FIG. 5 illustrates a circuit diagram of a low-pass filter circuit of the interface according to an embodiment of the present invention.

The low pass filter circuit 36 is configured to reduce the conversion of common-mode noise to differential noise within the frequency band of interest. Referring to FIG. 5, the low pass filter circuit 36 includes a capacitive component C4, connected in series at a first node to resistor R1 and at a second node to resistor R2. In one embodiment, C4 is a X2Y® capacitor, as described above with respect to FIG. 4, wherein a third node of capacitor C4 is connected to parallel resistors R3 and R4. The low pass filter circuit 36 further includes resistors R5 and R6, which limit the incoming impedance check current in the event of a circuit fault. In one non-limiting example, resistors R1 and R2 are high precision resistors each having a value of approximately 3.48 kΩ, and resistors R5 and R6 are approximately 1MΩ each to limit impedance check current in the event of a circuit fault. As will be described in further detail below with respect to FIG. 14, resistors R3 is bootstrapped so that the impedance to ground within the signal bandwidth of interest appears higher. When configured as shown in FIG. 5, the low pass filter circuit 36 provides a low-pass corner at approximately 21 KHz. However, it is to be appreciated that the low-pass corner of the low pass filter circuit 36 may vary depending on the input impedance presented to the interface 20 from the physiological sensors 24. The differential output of the low pass filter circuit 36 directly couples to an input of an instrumentation amplifier circuit 38, shown in FIG. 2, and illustrated in further detail in FIG. 6.

Figure 6:
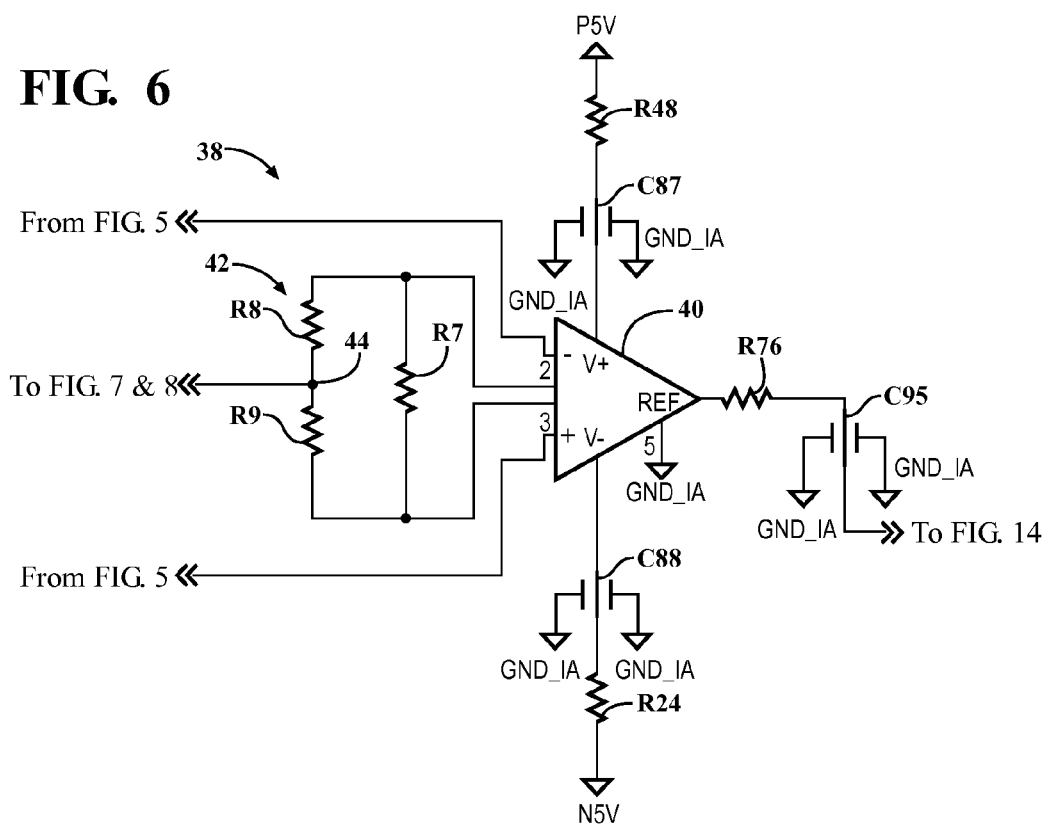
FIG. 6 illustrates a circuit diagram of an instrumentation amplifier circuit of the interface according to an embodiment of the present invention.

As set forth above, the instrumentation amplifier circuit 38 is configured to increase the amplitude of the bio-electric signals. As shown in FIG. 6, the differential output of the low pass filter circuit 36 is connected, respectively, to negative (−) and positive (+) input terminals of an amplifier 40. The gain of amplifier 40 is selected by a gain circuit 42, which in one embodiment, is a combination of resistors R7, R8 and R9, connected to pins 1 and 8 of the amplifier 40. As understood by one skilled in the art, the gain circuit 42 that includes resistors R7, R8 and R9, as shown in FIG. 6, is merely exemplary in that any number or configuration of resistors that are consistent with a desired gain may be used. In some cases, the gain circuit may be a single resistor or resistive component.

When configured as shown in FIG. 6, the instrumentation amplifier circuit 38 provides a gain of ten to the electrical signals passing there through. An output node 44 of the gain circuit 42 is coupled to an input filter bootstrap circuit 46 and to a unity gain buffer 48 (described below with respect to FIG. 8. Resistor R76 and capacitor C95 form a single stage passive low-pass filter with a corner of 2.4 KHz at the output of amplifier 40. Resistor R48 and capacitor C87 filter the P5V power rail feeding amplifier 40 to further improve the circuits' PSRR (power supply rejection ratio—ability of the amplifier 40 to reject variation on the power inputs that might affect the output). This corner frequency is approximately 800 Hz. Resistor R24 and capacitor C88 do the same for N5V feeding amplifier 40. The input bootstrap circuit 46 is shown in FIG. 2 as part of the interface circuit 22 and illustrated schematically in FIG. 7. The instrumentation amplifier circuit is referenced to circuit ground GND_IA.

Figure 7:
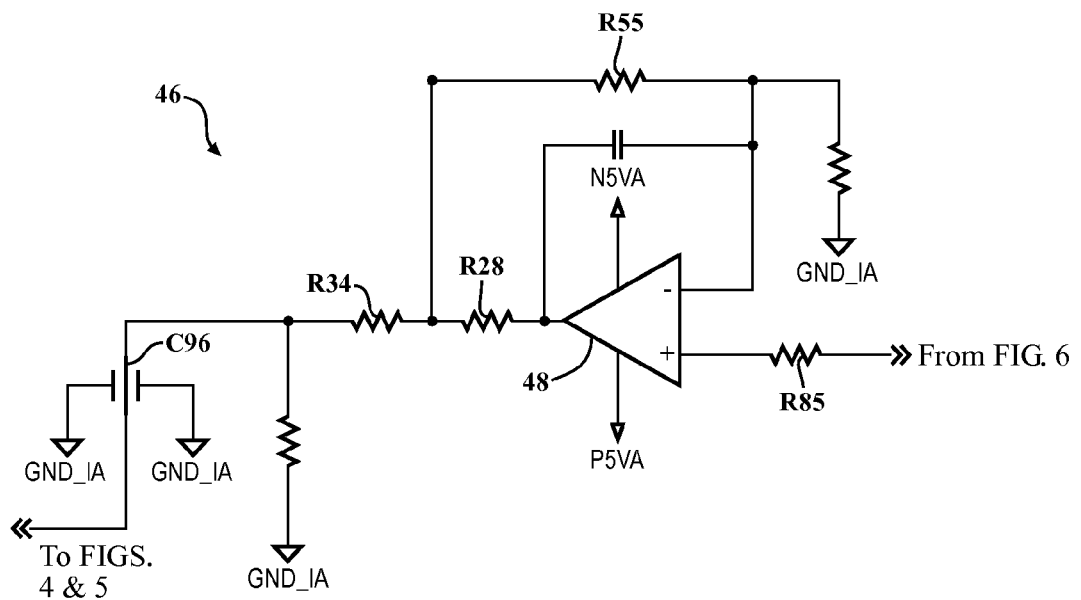
FIG. 7 illustrates a circuit diagram of a bootstrap circuit of the interface according to an embodiment of the present invention.

The input bootstrap circuit 46 is configured to attenuate noise and increase the effective input impedance at the input filter circuit 34 and at the instrumentation amplifier circuit 38 through the low pass filter circuit 36. Referring first to FIG. 7, input bootstrap circuit 46 includes an amplifier 48, referred to hereinafter as a bootstrap amplifier, which is referenced to circuit ground GND_IA. The signal provided at output node 44 of the gain network 42, which is also referred to as the common-mode signal, is input to the positive terminal of bootstrap amplifier 48. The input bootstrap circuit 46 includes a low-pass filter having a low-pass corner at approximately 800 Hz. As a result, the input bootstrap circuit 46 provides a unity-gain representation and low-pass filtering of the common-mode signal. Referring to FIG. 7, consider the node defined by the junction of R34, R28 and R55 as V'. There are two gains presented by this circuit, of which the DC gains are first considered. The first gain is defined as the gain between signal VCM_IA, which is the input to R85 (from FIGS. 6 and 8). This gain G1 is defined as $1+(R55/R29)=1.08$. The second gain G2 is defined as the gain between V' and VCM_AC (signal going from C96 to FIGS. 4 and 5). G2 is defined as $R36/(R36+R36)=0.924$. The product of $G1 \times G2=0.998$, which is essentially unit gain, meaning that the common-mode signal input into this circuit block through R85, is replicated within 1% as presented at the output of the circuit block through C96. The AC response must be considered as well, and requires a simple calculation of a first-order low-pass response defined by R36 and C96. The cutoff frequency $Fc=1/(2 \times PI \times R36 \times 2 \times C96)=1.7$ KHz. The end result is that low frequencies below Fc are presented to the networks of FIGS. 4 and 5 as a replica of the input to this block, effectively increasing the low-frequency effective CM impedance. As frequencies approach and pass Fc, the magnitude of the output signal decreases with respect to the input, which means that the networks of FIGS. 4 and 5 are not strongly boot-strapped at high frequencies, allowing high-frequency CM current to drain off through C96, reducing the high-frequency CM voltage presented to U1. As best shown in FIG. 2, the output of the input bootstrap circuit 46 is coupled to the input filter circuit 34 and at the instrumentation amplifier circuit 38 through the low pass filter circuit 36.

Referring to FIG. 4, the common mode (CM) input impedance at the input filter circuit 34 is increased by coupling the output of the input bootstrap circuit 46 to a third node C3C of capacitor C3. In other words, the input bootstrap circuit 46 is configured to force a lower end of the capacitor C3 to the same alternating current voltage as a top end of capacitor C3; thereby reducing CM current flow through capacitor C3 at low frequencies. In turn, capacitor C3 is effectively boot-strapped by capacitor C96 of the input bootstrap circuit 46, such that the effective CM impedance of capacitor C3 increases for low frequencies. Increasing the effective CM impedance at the input filter circuit 34, in effect, increases the effective input impedance at low frequencies for the instrumentation amplifier circuit 38. For higher frequencies, the input CM impedance is defined by balanced line capacitor C96 and the capacitive components of the input filter circuit 34. As such, residual high frequency energy passing through filters L1 and L2 are attenuated before reaching the amplifier 40, which is susceptible to high frequency content which may contaminate the electrical signal.

Referring to FIG. 5, the output of the input bootstrap circuit 46 is also coupled to the input of the low pass filter 36, and in particular, to input resistor R3. As a result, the input bootstrap circuit 46 increases the effective CM input impedance at the amplifier 40 for attenuating noise present in the electrical signals. Specifically, through resistor R3, the capacitor C4 is bootstrapped by the input bootstrap circuit 46. Mainly, the input bootstrap circuit 46 forces a lower end of the capacitor C4 to the same alternating current voltage as a top end of capacitor C4; thereby reducing CM current flow through capacitor C4 at low frequencies. In turn, capacitor C4 is effectively bootstrapped by C96 such that the effective CM impedance of capacitor C4 increases for low frequencies. Furthermore, the input bootstrap circuit 46 is also configured to increase an effective CM impedance of resistor R3. Specifically, the input bootstrap circuit 46 forces a lower end of resistor R3 to the same alternating current voltage as a top end of resistor R3; thereby reducing CM current flow through resistor R3 at low frequencies.

When configured as set forth above and as shown in the Figures, the effective common-mode input impedance at the input of the instrumentation amplifier circuit 40 is approximately 376 kΩ at direct current. However, for low-frequency alternating current signals, and particularly for U.S. line signals, which have noisy frequencies ranging between 50-60 Hz, the input bootstrap circuit 46 increases the effective input impedance at low frequencies; thereby attenuating the noise present in the electrical signals within the bandwidth of interest. For higher frequencies, the effective input impedance at the instrumentation amplifier circuit 40 is not effectively increased by input bootstrap circuit 46. When configured as shown in the Figures, the input bootstrap circuit 46 provides an effective input impedance in excess of 100 MΩ at line frequencies. Increasing the effective input impedance at low frequencies also reduces mode conversion with impedance mismatches at sensors. In other words, the input bootstrap circuit 46 compensates for mismatches in input impedance by bootstrapping components of the interface 20 to increase the effective input impedance of the overall system thereby reducing the effect of mismatches.

Figure 8:
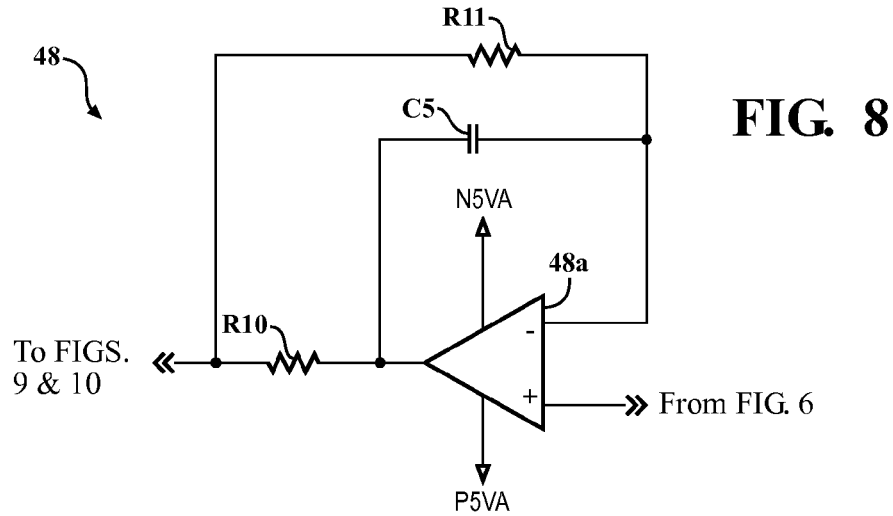
FIG. 8 illustrates a circuit diagram of a unity gain buffer circuit of the interface according to an embodiment of the present invention.

Referring back to FIG. 2, in addition to the common-mode signal at the output node 44 of the gain circuit 42 being coupled to the input filter bootstrap circuit 46, the common-mode signal is also coupled to a positive input terminal of the unity gain buffer 48, shown schematically in FIG. 8. The unity gain buffer 48 includes an amplifier 48a having an output resistor R10 and a feedback loop consisting of a resistor R11 and a capacitor C5. The output of the unity gain buffer 48 at node 50 is coupled to a common-mode cancellation amplifier circuit 52 and an inverter circuit 54. The unity gain buffer circuit 48 replicates the common-mode signal; thereby isolating the instrumentation amplifier circuit 38 from the common-mode cancellation amplifier circuit 52. As such, the unity gain buffer circuit 48 prevents noise from the operation of the common-mode cancellation amplifier circuit 52 from back flowing and disturbing the operation of the instrumentation amplifier circuit 38.

Figure 9:
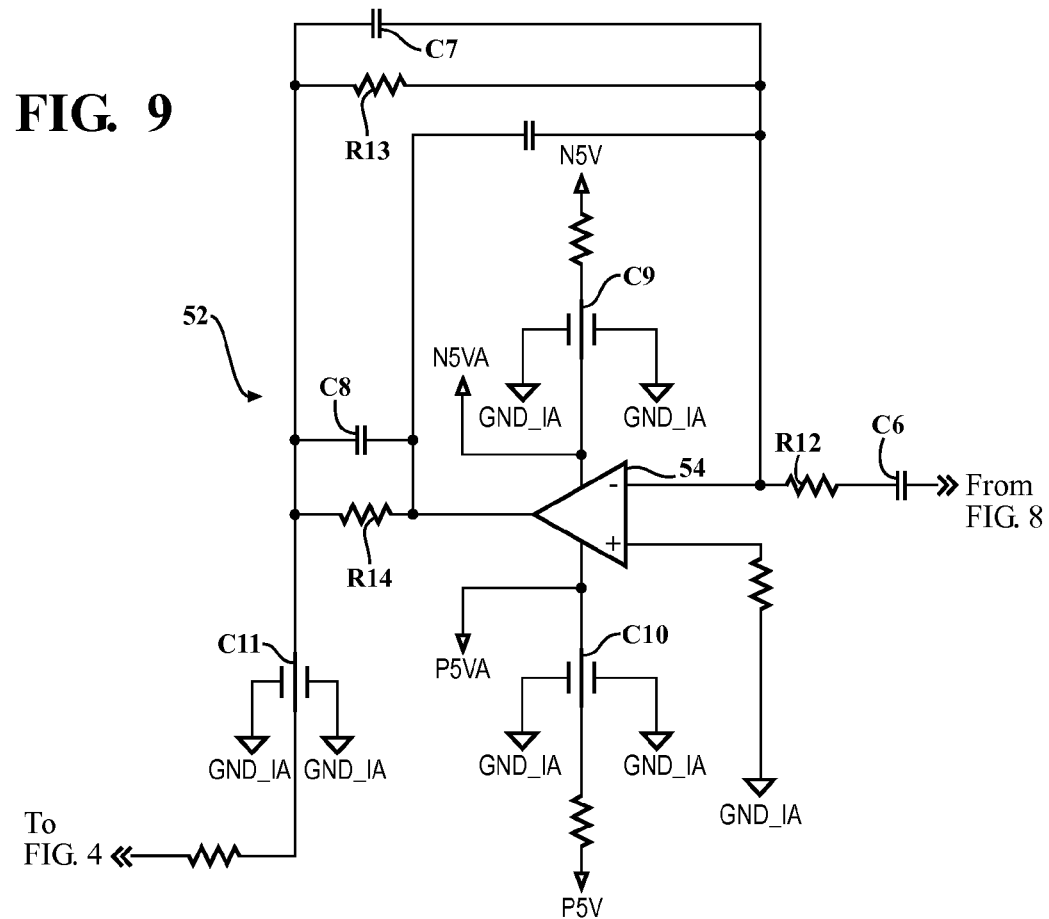
FIG. 9 illustrates a circuit diagram of a common-mode cancellation amplifier circuit of the interface according to an embodiment of the present invention.

The common-mode cancellation amplifier circuit 52 reduces common-mode signal noise present in the electrical signals. In other words, the common-mode cancellation amplifier circuit 52 effectively attenuates common-mode signal noise that might otherwise appear in the resulting electrical signal which is digitized by the processing system 32. Referring to FIG. 9, the common-mode cancellation amplifier circuit 52 includes a high-pass filter circuit having capacitor C6 and resistor R12 and initially conditions the common-mode signal provided by the unity gain buffer circuit 48. The common-mode cancellation amplifier circuit 52 also includes a low-pass filter and gain stage operatively coupled to the high-pass filter circuit. The low-pass filter includes capacitor C7 and resistor R13 and the gain stage has inverting amplifier 54. Resistor 14 at the output of amplifier 54 limits the output of direct current from the gain stage to safe levels in the event of a single-fault condition. Simultaneously, capacitor C8 provides low frequency alternating current impedance between inverting amplifier 54 and the sensors 24. Capacitors C9 and C10 are coupled to an input of inverting amplifier 54 and are referenced to GND_IA, while capacitor C11 is coupled to an output of inverting amplifier 54 and is referenced to GND_IA.

The common-mode cancellation amplifier circuit 52 outputs a reference signal (REF) for cancelling common-mode voltage present at the sensors 24. The reference signal is an inverted representation of the common-mode signal which is band-pass filtered approximately at corners 0.85 Hz to 850 Hz. The reference signal is supplied back to the sensors 24 through the front-end connector 30 for providing effective common-mode cancellation within the bandwidth of interest between 2 Hz-480 Hz. The common-mode cancellation amplifier circuit 52 is configured such that an effective output impedance of the reference signal is very low. Such low effective output impedance serves to improve common-mode cancellation of noise that would otherwise be impressed upon the electrical signal due to differences in alternating current potential between the patient 26 and the monitoring device 10. These potential differences occur because the patient 26, the monitoring device 10, and other patient connected equipment each have varying degrees of capacitive coupling between alternating current power supplies and earth ground.

Figure 10:
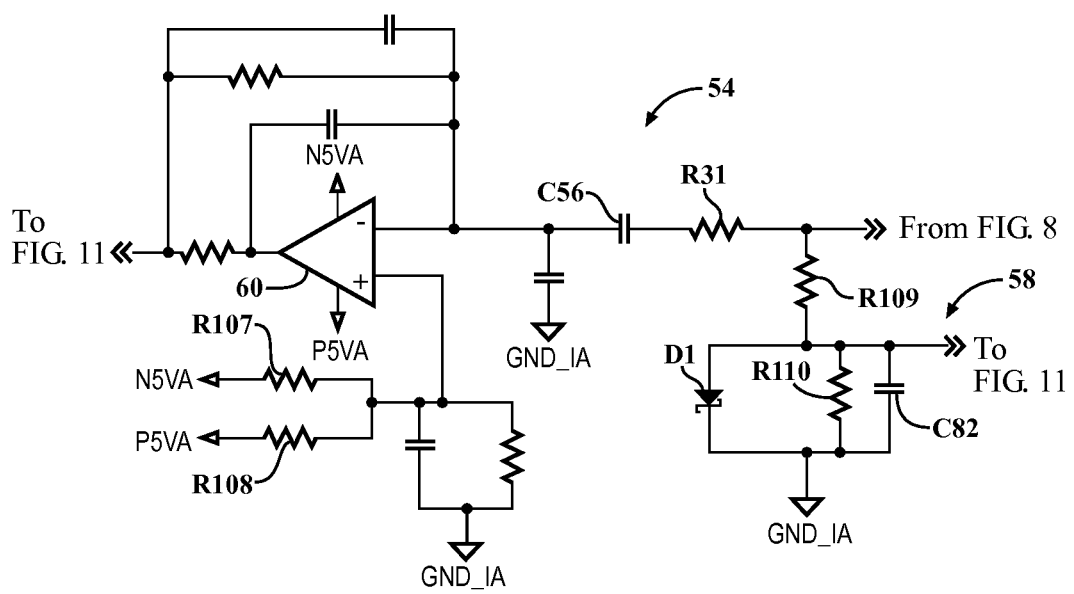
FIG. 10 illustrates a circuit diagram of an inverter circuit of the interface according to an embodiment of the present invention.

Referring now to FIG. 10, the inverter circuit 54 is configured to provide an inverted representation of the common-mode signal to the impedance check circuit 56. The inverter circuit 54 extracts the direct current component of the buffered common-mode signal through a resistor-capacitor network 58, which includes diode D1. The direct current component of the buffered common-mode signal is transmitted from the resistor-capacitor network 58 of the inverter circuit 48 to the impedance check circuit 56. The inverter circuit 54 also includes an inverter amplifier stage and low-pass filter for inverting and conditioning the buffered common-mode signal. The inverter amplifier stage has amplifier 60 at its core and outputs an inverted and buffered common-mode signal to the impedance check circuit 56. The inverted and buffered common-mode signal has a bandwidth of approximately 3.4 KHz. The resistor-capacitor network 58 and inverter amplifier stage of the inverter circuit 54 are referenced to circuit ground GND_IA.

Figure 11:
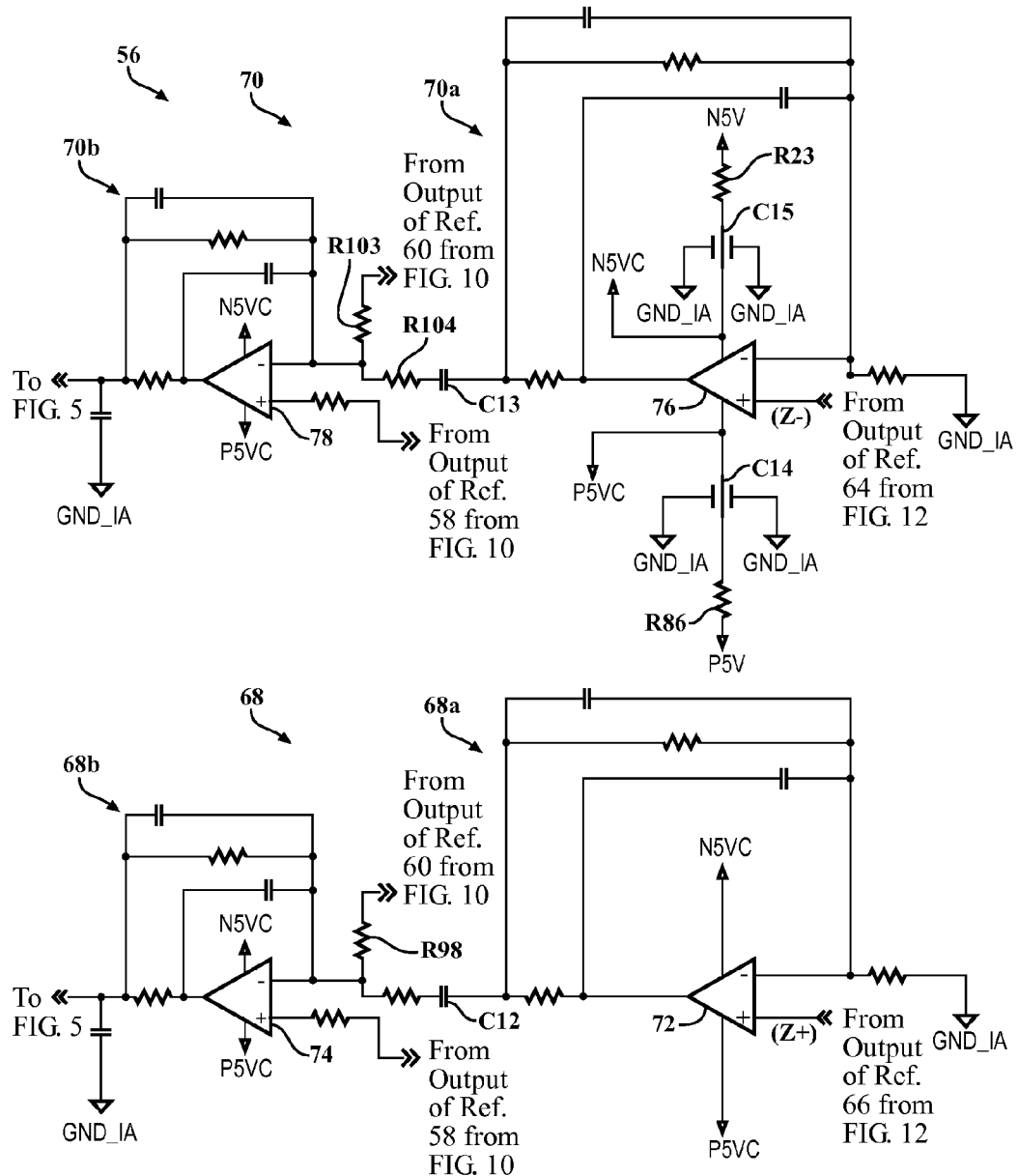
FIG. 11 illustrates a circuit diagram of an impedance check circuit of the interface according to an embodiment of the present invention.
Figure 12:
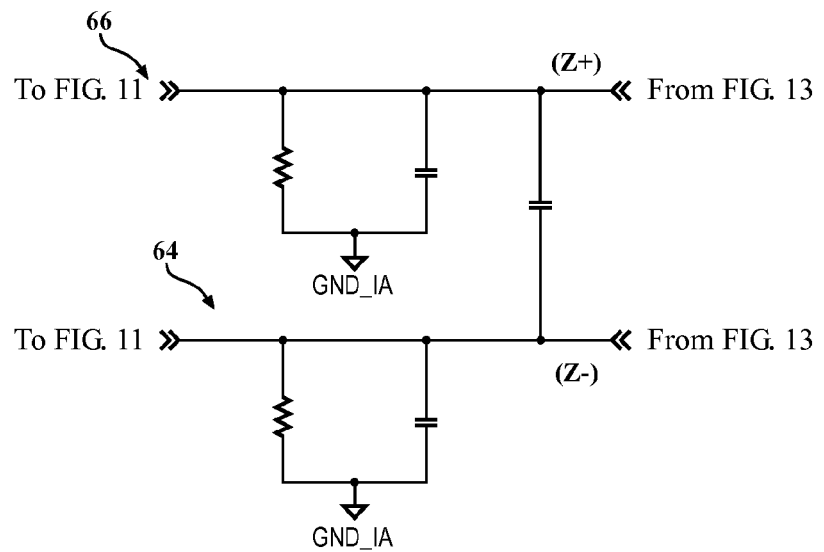
FIG. 12 illustrates a circuit diagram a resistor-capacitor network of the impedance check circuit according to an embodiment of the present invention.
Figure 13:
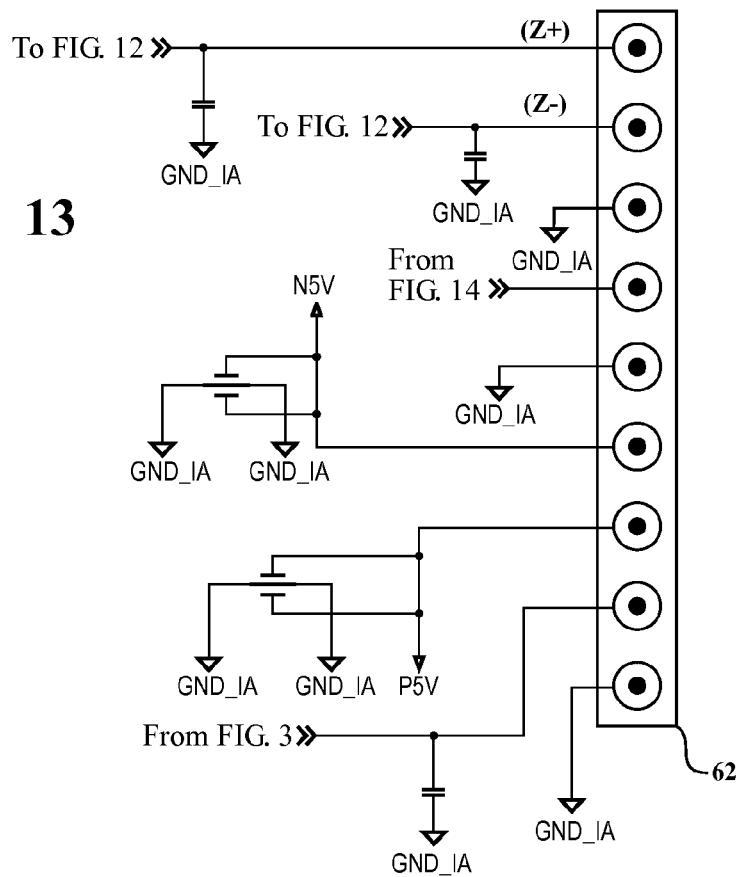
FIG. 13 illustrates a circuit diagram a back-end connector of the interface according to an embodiment of the present invention.

Referring to FIG. 11, the impedance check circuit 56 receives impedance check signals from the processing system 32 of the monitoring device 10. The impedance check signals (Z+) and (Z−) are provided by the processing system 32 to the interface 22 through a back-end connector 62, as shown in FIGS. 2 and 13. In order to reduce undesired artifact due to physical movement of the monitoring device 10, the impedance check circuit 56 includes a resistor-capacitor network 64, 66, shown separately in FIG. 12, for filtering each of the impedance check signals, (Z+) and (Z−), respectively. The resistor-capacitor networks 64, 66 are also configured to provide minimal impedance to circuit ground GND_IA. As shown in FIG. 12, the resistor-capacitor network 64, 66 for each of the impedance check signals (Z+) and (Z−) is operatively connected to the back-end connector 62.

Referring back to FIG. 11, the impedance check circuit 56 includes an impedance check gain and filter stage 68, 70 for raising the gain and conditioning each impedance check signal (Z+) and (Z−), respectively, which passes through each of the resistor-capacitor networks 64, 66. Each of the impedance check gain and filter stages 68, 70 includes a first impedance check amplification stage 68a, 70a, and a second impedance check amplification stage 68b, 70b, respectively. In particular, impedance check signal (Z+) passes through the first impedance check amplification stage 68a having amplifier 72 at its core before passing to the second impedance check amplification stage 68b having amplifier 74 at its core. The impedance check signal (Z+) is alternating current coupled between the first and second impedance amplification stages 68a, 68b across capacitor C12. Likewise, impedance check signal (Z−) passes through the first impedance check amplification stage 70a having amplifier 76 at its core before passing to the second impedance check amplification stage having amplifier 78 at its core. The impedance check signal (Z−) is alternating current coupled between the first and second impedance amplification stages 70a, 70b across capacitor C13.

Amplifier 76 of the first impedance check amplification stage 70a has balanced line capacitors C14 and C15 operatively coupled to an input of amplifier 76 for reducing electromagnetic interference of the electrical signal. Capacitors C14 and C15 are power rail filters in conjunction with R23 and R86 respectively. These serve the same purpose and have the same bandwidth as the power supply filters described in Paragraph 36. Each of the impedance check gain and filter stages 68, 70 further includes a low-pass filter to reduce high-frequency contamination of the electrical signal. When configured as shown in FIG. 11, the low-pass filters provide a low-pass corner at approximately 41 Hz.

The impedance check circuit 56 enables automated checking of a physical interface between the sensors 24 and the patient 26. Individual or synchronous application of the impedance check signals (Z+) and (Z−), amplification and conditioning by the impedance check gain and filter stages 68, 70, and analysis by the processing system 32 enables an estimation of impedances formed by the sensors 24 and the skin of the patient 26.

The amplifiers 74, 78 of each respective second impedance check amplification stage 70b, 70a combine the impedance check signal from the processing system 32 with the direct current component of the buffered common-mode signal and the inverted buffered common-mode signal as provided from the inverter circuit 54. The modified impedance check signals are then coupled to the signal path of the differential signals (+) and (−) of the electrical signals through resistors R5 and R6; thereby completing presentation of the impedance check signal to the physical interface between the sensors 24 and the patient 26. This circuit also provides increased CM impedance through bootstrapping.

Figure 14:
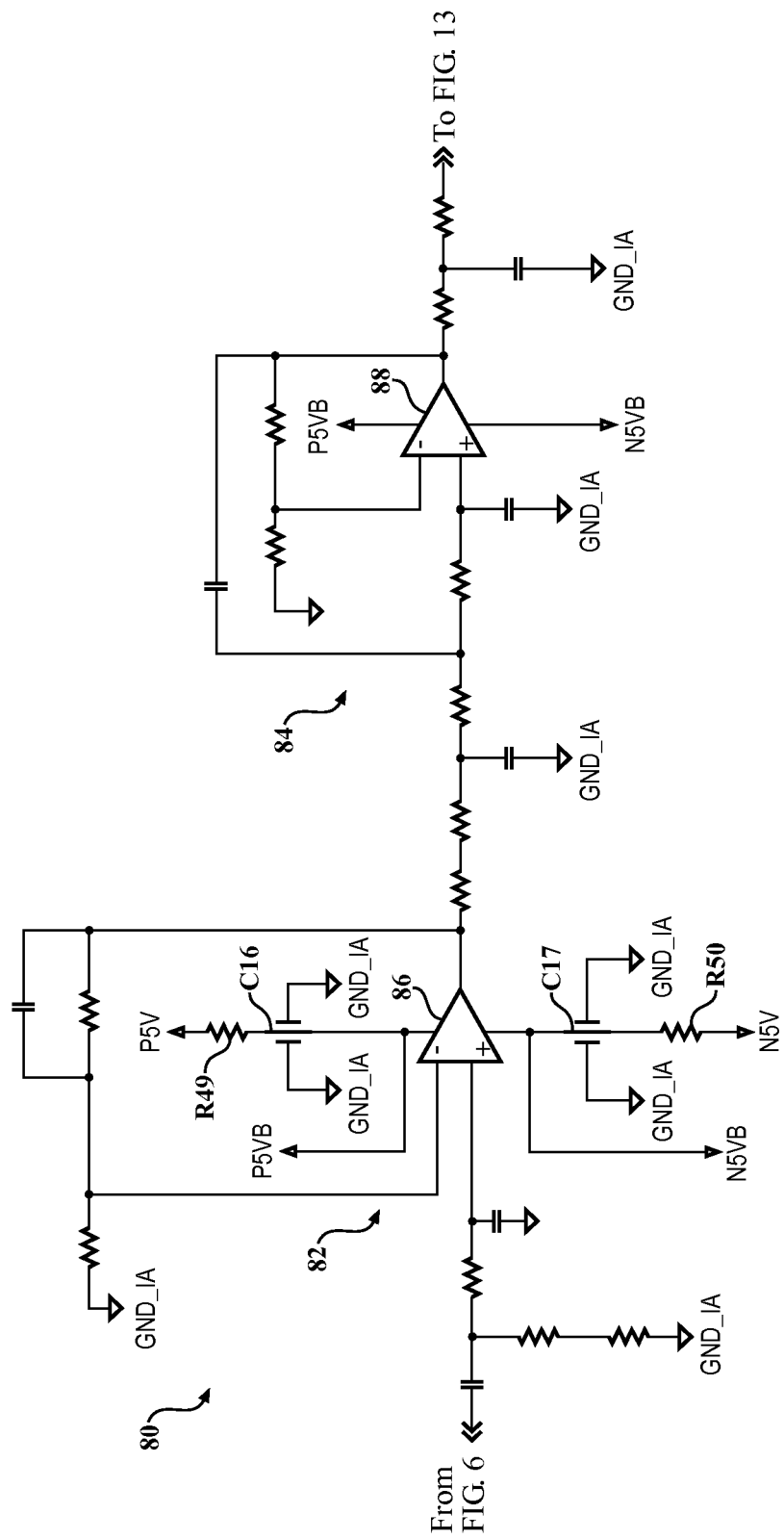
FIG. 14 illustrates a circuit diagram a gain amplifier circuit of the interface according to an embodiment of the present invention.

The interface 22 also includes a second stage gain amplifier circuit 80 coupled between the instrumentation amplifier circuit 38 and the processing system 32. After the electrical signal is amplified by the instrumentation amplifier circuit 38, the amplified signal is then passed to the second stage gain amplifier circuit 80. The second stage gain amplifier circuit 80 provides a bandpass filter and gain function for the representations of the electrical signals. As shown in FIG. 14, the second stage gain amplifier circuit 80 includes a first amplification stage 82 and a second amplification stage 84. The first amplification stage 82 includes resistive and capacitive components and an amplifier 86 at its core. Specifically, balanced line capacitors C16 and C17 are operatively coupled to an input of amplifier 86. C16 and C17, in conjunction with R49 and R50, filter the incoming power rail as previously noted in Paragraphs 36 and 47. The electrical signal passes through the second amplification stage 84 immediately after passing through the first amplification stage 82. The second amplification stage 84 includes resistive and capacitive components and an amplifier 88 at its core. When configured as shown in FIG. 14, the second stage gain amplifier circuit 80 alters the amplitude of the electrical signal to provide a gain of approximately 60× for the first amplification stage 82 and a gain of approximately 10× for the second amplification stage 84. The second stage gain amplifier circuit 80 provides passband corners of approximately 2 Hz and 1000 Hz. The resulting electrical signal is then routed to the back-end connector 62 and ultimately passed on to the processing system 32 through the shielded cable, as shown in FIG. 13.

While bootstrapping the input filter circuit 38 and low pass filter 36 by the input bootstrap circuit 46 provides an increase in the effective input impedance for the alternating current component of the electrical signal, bootstrapping the impedance check circuit 52 provides an increase in the effective input impedance for the direct current component of the electrical signal. As mentioned above, the modified impedance check signals outputted from the impedance check circuit 52 include the direct current component of the buffered common-mode signal and an inverted representation of the buffered common-mode signal. The modified impedance check signals are direct current coupled to resistors R5 and R6 which are effectively bootstrapped by the modified impedance check signals. In turn, the impedances of R5 and R6 are effectively increased at low frequency. The inverted CM signal through R103 and R98 is inverted again (to original phase) by amplifiers 78 and 74. This bootstraps R5 and R6.

Referring back to FIG. 6, output node 44 has a DC component that is dependent upon the particular instrumentation amplifier 40 used. In this embodiment, the LT1167 generates a voltage that is approximately 0.48 VDC less than the common-mode input voltage at input pins 2 and 3 (−0.48 VDC with normal input conditions). This CM component is passed unchanged through the amplifier in FIG. 8 to output node 50. In turn, this signal is input to FIG. 10 (still node 50), and passed through a low-pass filter and divider network composed of R109, R110, and C82. The DC component of the CM signal is attenuated by a factor of 0.55 (R110/(R109+R110)), and the corner frequency is approximately 0.16 Hz. Diode D1 prevents the signal output to FIG. 11 from exceeding GND_IA and assures that the latching operation described in paragraph 57 is achieved toward the negative power supply rail. A different instrumentation amplifier might require D1 to be reversed if the generated common-mode voltage is greater than the input common-mode voltage.

Referring again to FIG. 10, a DC component is also introduced to the output of the amplifier 60 in FIG. 11 through the network connected to pin 3 of this same amplifier. Either R107 or R108 are populated, depending upon the particular DC offset desired (depending upon particular characteristics of the instrumentation amplifier 40). In this embodiment, R107 is populated with 100K ohm. The voltage input to pin 3 of amplifier 60 is approximately −5.0×(R54/(R54+107))=−0.45 VDC.

The AC component of the input signal to FIG. 8 is passed through a high-pass filter composed of R31 and C56, with a corner frequency of approximately 1.6 Hz. In addition, the R31 value of 102 Kohm, when considered in the gain equation for amplifier 60, causes the AC output of 60 to be passed with slightly less than unity gain G≈R54/R31=0.98.

The combined DC and AC components from amplifier 60 in FIG. 10 are also passed to FIG. 11 to R103 and R98. The DC component described previously in paragraph 43 is passed to FIG. 11 to R102 and R98. These signal components in turn are combined in amplifiers 74 and 78, along with the impedance check signal as described previously in paragraph 49.

Under normal operating conditions with a PIC connected to a sensor which is in turn connected to a patient, there is a relatively low-impedance DC path from the (REF) electrode through the (−) and (+) electrodes, terminating at the inputs to instrumentation amplifier U1. The normal mode steady state DC potential across the (−) and (+) sensors to the (REF) sensor is defined by the DC networks previously described, and is approximately −70 mV, which results in a current through the sensors of approximately 70 nA. In the event that a sensor is not connected to the PIC or the (REF) electrode is not connected to a patient, this DC path becomes very high impedance, and is driven by the outputs of amplifiers 78 and 74 in FIG. 11 into the network of FIG. 5. Under these conditions, the DC component of amplifiers 78 and 74 is determined by a positive DC feedback loop that will eventually (within seconds) drive the inputs of the instrumentation amplifier 40 beyond the maximum negative DC common-mode input range of amplifier 40, causing the inputs to latch. This will result in the output of amplifier 40 going to 0 VDC and insensitive to further input conditions until a low-impedance path is reestablished to the inputs of amplifier 40.

The effect of this condition is that in the event of no sensor connected between the PIC 20 and the patient 26, or the (REF) electrode becoming disconnected, the output of the PIC 20 will be zero volts under all input conditions, including during impedance checking. This condition is detectable by the device 10 firmware as an error condition.

In order to assure that the desired latch up condition is achieved, the common-mode cancellation path through the impedance check circuit must be tuned such that it is stable and does not oscillate with respect to the common-mode cancellation path through input filter capacitors C3 (FIG. 4) and C4 (FIG. 5). Reduction of the AC common-mode signal gain as described in paragraph 55 assures that the system will be stable in the event of a sensor or (REF) electrode disconnect, at the price of slightly reduced low-frequency common-mode rejection.

In the event that one or both of the signal electrodes (−) and (+) would become disconnected from the patient, the high input impedance formed by the bootstrap circuits assures that an impedance check stimulus presented as described previously in paragraph 48 in these conditions will result in very little current flow through the disconnected electrode, resulting in an impedance check signal that is large and indicative of an open electrode. This impedance check signal is defined by a voltage divider in FIG. 5 formed by R5 (or R6) and the combined electrode/skin impedance. In the case of a disconnected electrode, the impedance of R5 (or R6) is very small compared to that of the open circuit, which results in the full scale impedance check signal being presented to the input of the instrumentation amplifier.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An interface for receiving an electrical signal representative of a condition of a patient and for conveying representations of the electrical signal to a processing system, said interface comprising:
at least one amplifier circuit configured to alter an amplitude of the electrical signal; and
a common-mode cancellation amplifier circuit coupled to said at least one amplifier circuit and configured to reduce common-mode signal noise in the electrical signal;
a bootstrap circuit coupled to said at least one amplifier circuit and configured to increase an effective input impedance at an input of said at least one amplifier circuit; and
an impedance check circuit coupled to said at least one amplifier circuit, wherein said impedance check circuit is configured to be coupled to the processing system and enable automated checking of a physical interface between at least one sensor and the patient and to receive impedance check signals from the processing system.

2. The interface of claim 1 further comprising an input filter circuit coupled to said at least one amplifier circuit.

3. The interface of claim 2 wherein said input filter circuit includes at least one capacitive component configured to reduce differential and common-mode radio frequency interference in the electrical signal.

4. The interface of claim 3 wherein said bootstrap circuit is coupled to said at least one capacitive component.

5. The interface of claim 3 wherein said at least one capacitive component includes at least one balanced line capacitor.

6. The interface of claim 1 wherein said impedance check circuit includes a low-pass filter circuit configured to filter said impedance check signals, and first and second impedance check amplification stages configured to amplify each of said impedance check signals.

7. The interface of claim 6 wherein said impedance check circuit further includes a resistor-capacitor network for each of said impedance check signals with each of said resistor-capacitor networks being coupled to an input of each of said first and second impedance check amplification stages, wherein said resistor-capacitor networks are configured to filter and provide low impedance to ground for each of said impedance check signals.

8. An interface for receiving an electrical signal representative of a condition of a patient and for conveying representations of the electrical signal to a processing system, said interface comprising:
at least one amplifier circuit configured to alter an amplitude of the electrical signal and provide a common-mode signal; and
a common-mode cancellation amplifier circuit coupled to said at least one amplifier circuit and configured to reduce common-mode signal noise in the electrical signal;
a bootstrap circuit coupled to said at least one amplifier circuit and configured to increase an effective input impedance at an input of said at least one amplifier circuit; and
an impedance check circuit, wherein said common-mode cancellation amplifier circuit, said bootstrap circuit, and said impedance check circuit are configured to receive the common-mode signal.

9. The interface of claim 8 wherein said bootstrap circuit includes a bootstrap amplifier circuit configured to provide a unity-gain representation and low-pass filtering of said common-mode signal.

10. The interface of claim 1 wherein said at least one amplifier circuit includes a gain setting network configured to set a gain for said at least one amplifier circuit.

11. The interface of claim 10 wherein said gain setting network is configured to provide a common-mode signal.

12. The interface of claim 1 wherein said common-mode cancellation amplifier circuit includes a high-pass filter circuit coupled to a low-pass filter and a gain stage, wherein said low-pass filter and said gain stage are configured to output a reference signal that cancels a common-mode voltage associated with at least one sensor.

13. The interface of claim 1 including a low-pass filter circuit coupled to said bootstrap circuit and said at least one amplifier circuit wherein said low-pass filter circuit includes at least one resistive component and at least one capacitive component.

14. The interface of claim 13 wherein said at least one capacitive component includes at least one balanced line capacitor.

15. The interface of claim 1 wherein said interface is an analog interface.

\* \* \* \* \*